US008921261B2

(12) United States Patent
Lee et al.

(10) Patent No.: US 8,921,261 B2
(45) Date of Patent: Dec. 30, 2014

(54) CATALYST FOR SYNTHESIZING GLYCEROL CARBONATE FROM GLYCEROL, METHOD FOR PRODUCING THE CATALYST AND METHOD FOR SYNTHESIZING GLYCEROL CARBONATE FROM GLYCEROL USING THE CATALYST

(71) Applicant: Korea Institute of Industrial Technology (KITECH), Chungcheongnam-do (KR)

(72) Inventors: Man Sig Lee, Kyeongsangnam-do (KR); Jae Ho Baek, Busan (KR)

(73) Assignee: Korea Institute of Industrial Technology (KITECH), Chungcheongnam-Do (KR)

(*) Notice: Subject to any disclaimer, the term of this patent is extended or adjusted under 35 U.S.C. 154(b) by 31 days.

(21) Appl. No.: 13/718,610

(22) Filed: Dec. 18, 2012

(65) Prior Publication Data
US 2013/0267715 A1    Oct. 10, 2013

(30) Foreign Application Priority Data

Apr. 10, 2012    (KR) .......................... 10-2012-0037564

(51) Int. Cl.
| | | |
|---|---|---|
| B01J 23/02 | (2006.01) | |
| B01J 23/06 | (2006.01) | |
| C07D 407/00 | (2006.01) | |
| C07D 493/00 | (2006.01) | |
| C07D 317/08 | (2006.01) | |
| C07D 317/36 | (2006.01) | |
| B01J 37/03 | (2006.01) | |
| B01J 37/08 | (2006.01) | |
| B01J 37/10 | (2006.01) | |
| B01J 35/10 | (2006.01) | |

(52) U.S. Cl.
CPC ............... *B01J 23/06* (2013.01); *C07D 317/36* (2013.01); *B01J 37/031* (2013.01); *B01J 37/08* (2013.01); *B01J 37/10* (2013.01); *B01J 35/1014* (2013.01); *B01J 35/1019* (2013.01)
USPC ........................................... 502/342; 549/229

(58) Field of Classification Search
USPC ........................................ 502/342; 549/229
See application file for complete search history.

(56) References Cited

U.S. PATENT DOCUMENTS

| | | | | |
|---|---|---|---|---|
| 2,556,280 A | * | 6/1951 | Kearby | ............... 208/136 |
| 5,028,652 A | * | 7/1991 | Smutny et al. | ............... 524/434 |

(Continued)

FOREIGN PATENT DOCUMENTS

| | | | | |
|---|---|---|---|---|
| JP | 06-329663 | * | 11/1994 | .......... C07D 317/36 |
| KR | 10-2013-0121603 | * | 6/2013 | ............ C07C 69/96 |

(Continued)

OTHER PUBLICATIONS

"Chemicals from biomass: Synthesis of glycerol carbonate by transesterification and carbonylation with urea with hydrotalcite catlysts. The role of acid-base pairs," Maria J. Climent et al. Journal of Catalysis 269 (2010), pp. 140-149.*

*Primary Examiner* — Patricia L Hailey
(74) *Attorney, Agent, or Firm* — Alston & Bird LLP

(57) ABSTRACT

Disclosed are a catalyst for synthesizing glycerol carbonate from glycerol and a method for producing the catalyst. The method includes adding an aqueous NaOH solution, an aqueous KOH solution, or a mixture of an aqueous $NH_4(OH)$ solution and an aqueous NaOH solution to an aqueous solution of a mixture of zinc nitrate and aluminum nitrate, aging the mixture, filtering and washing the aged mixture to obtain a solid, and calcining the solid under an oxygen, nitrogen or helium atmosphere. The use of the catalyst enables the synthesis of glycerol carbonate from glycerol and urea with high conversion rate, selectivity and yield. Further disclosed is a method for synthesizing glycerol carbonate from glycerol using the catalyst.

12 Claims, 6 Drawing Sheets

(56) References Cited

U.S. PATENT DOCUMENTS

| | | | | |
|---|---|---|---|---|
| 6,025,504 | A * | 2/2000 | Claude et al. | 549/229 |
| 6,495,703 | B1 * | 12/2002 | Okutsu et al. | 549/229 |
| 2011/0092730 | A1 * | 4/2011 | Bazer-Bachi et al. | 560/129 |
| 2013/0165729 | A1 * | 6/2013 | Selvanathan et al. | 585/663 |

FOREIGN PATENT DOCUMENTS

| | | | | |
|---|---|---|---|---|
| KR | 10-1307559 | * | 9/2013 | C07D 317/36 |
| KR | 10-1389545 | * | 11/2013 | C07C 69/96 |
| KR | 10-2014-0014563 | * | 2/2014 | C07D 317/14 |

* cited by examiner

CATALYST FOR SYNTHESIZING GLYCEROL CARBONATE FROM GLYCEROL, METHOD FOR PRODUCING THE CATALYST AND METHOD FOR SYNTHESIZING GLYCEROL CARBONATE FROM GLYCEROL USING THE CATALYST

CROSS-REFERENCE TO RELATED APPLICATION

This application claims priority from Korean Patent Application No. 10-2012-0037564, filed Apr. 10, 2012, which is incorporated by reference herein in its entirety.

BACKGROUND OF THE INVENTION

1. Field of the Invention

The present invention relates to a catalyst for synthesizing glycerol carbonate from glycerol, a method for producing the catalyst, and a method for synthesizing glycerol carbonate from glycerol using the catalyst. More specifically, the present invention relates to a catalyst for synthesizing glycerol carbonate from glycerol and urea with high conversion, selectivity and yield, a method for producing the catalyst, and a method for synthesizing glycerol carbonate from glycerol using the catalyst.

2. Description of the Related Art

In recent years, as fossil fuels have become more expensive, biodiesel, along with bioethanol, has attracted attention as a liquid fuel energy source that can replace fossil fuels. Considerable amounts of waste liquids are generated from biodiesel production processes. The waste liquids include a high concentration of glycerol as a by-product and account for about 10% of the biodiesel production. Such by-products containing glycerol may cause secondary pollution. Particularly, a considerable cost is required to treat a large amount of waste glycerol, leading to low economic efficiency of biodiesel production processes. Under these circumstances, there is a need to convert waste glycerol, a by-product of biodiesel production processes, to high value-added glycerol derivatives and to develop new applications of the glycerol derivatives.

Glycerol can be converted to glycerol derivatives, such as glycerol carbonate, 1,3-propanediol, glycolic acid, propylene glycerol, glycidol, propanol and glyceric acid, by chemical/biological methods. Of these, glycerol carbonate (GC, 4-hydroxymethyl-1,3-dioxolan-2-one) is a compound that has biodegradability, low irritability, high boiling point, non-volatility, and moisturizing ability. Glycerol carbonate is a solvent or an intermediate for medical applications and is considered a promising new replacement for propylene carbonate. Glycerol carbonate can also be used as a main component for coatings, paints, detergent additives, vegetable lubricants, lithium battery additives, cosmetic humectants, and gas separation membranes.

For the purpose of increasing the value of glycerol, a great deal of research has been conducted on methods for converting glycerol to glycerol carbonate. Many methods are known for converting glycerol to glycerol carbonate, for example, a method including the reaction of glycerol with a carbonate compound, such as ethylene carbonate or dimethyl carbonate, a method including the reaction of glycerol with carbon dioxide, and a method including the reaction of glycerol with urea. The method including the reaction with a carbonate compound is unfavorable in terms of competitiveness because of the use of the existing carbonate compound, and the method including the reaction with carbon dioxide is environmentally friendly but has the disadvantage of low yield. In contrast, the method including the reaction with cheap inexpensive and environmentally friendly urea as a raw material is receiving much attention due to its high commercial viability.

In methods for synthesizing glycerol carbonate using urea, conversion rate of glycerol, selectivity to glycerol carbonate, and final reaction yield of glycerol carbonate are dependent on reaction catalysts. Thus, there is a need to develop a method for efficiently synthesizing glycerol carbonate using a more highly active reaction catalyst.

In view of this situation, the present inventors have found that a catalyst suitable for the synthesis of glycerol carbonate from glycerol can be produced when an aqueous NaOH solution, an aqueous KOH solution, or a mixture of an aqueous $NH_4(OH)$ solution and an aqueous NaOH solution is added to an aqueous solution of a mixture of zinc nitrate and aluminum nitrate, the mixture is aged, the aged mixture is filtered and washed to obtain a solid, and the solid is calcined under an oxygen, nitrogen or helium atmosphere. The present inventors have also found that the use of the catalyst enables the synthesis of glycerol carbonate from glycerol and urea with high conversion, selectivity and yield. Based on these findings, the present invention has been accomplished.

SUMMARY OF THE INVENTION

It is an object of the present invention to provide a method for producing a catalyst suitable for the synthesis of glycerol carbonate from glycerol.

It is a further object of the present invention to provide a catalyst for synthesizing glycerol carbonate from glycerol, which is produced by the method.

It is another object of the present invention to provide a method for synthesizing glycerol carbonate from glycerol using the catalyst.

According to an aspect of the present invention, there is provided a method for producing a catalyst suitable for the synthesis of glycerol carbonate from glycerol, the method including 1) preparing an aqueous solution of a mixture of zinc nitrate and aluminum nitrate (step 1), 2) adding an aqueous NaOH solution, an aqueous KOH solution, or a mixture of an aqueous $NH_4(OH)$ solution and an aqueous NaOH solution to the aqueous solution of the metal nitrate mixture (step 2), 3) aging the mixture of step 2 (step 3), 4) filtering and washing the aged mixture to obtain a solid (step 4), and 5) calcining the solid under an oxygen, nitrogen or helium atmosphere (step 5), wherein the ratio of the density of acid sites to that of base sites on the catalyst surface is from 0.3 to 2.0.

A catalyst produced by the method of the present invention is in the form of a binary metal oxide having both acid sites and base sites thereon. The presence of acid sites and base sites improves the activity and economic efficiency of a final catalyst.

In step 1, an aqueous solution of a mixture of zinc nitrate and aluminum nitrate is prepared. That is, zinc nitrate and aluminum nitrate are dissolved in water to prepare an aqueous solution of the metal nitrates.

The method of the present invention is characterized by the production of a catalyst in the form of a binary metal oxide composed of zinc (Zn) as a base element and aluminum (Al) as a secondary element.

In step 1, it is preferred to adjust the mixing molar ratio of the zinc to the aluminum to 7:3 to 8:2 taking into consideration the effects of a final catalyst, including conversion rate of glycerol, selectivity to glycerol carbonate, and the resulting yield of glycerol carbonate.

In the present invention, the zinc nitrate and the aluminum nitrate may be in the form of hydrates. Specifically, zinc nitrate hexahydrate, $Zn(NO_3)_2 \cdot 6H_2O$, may be used as the zinc nitrate, and aluminum nitrate nonahydrate, $Al(NO_3)_3 \cdot 9H_2O$, may be used as the aluminum nitrate.

In step 2, an aqueous NaOH solution, an aqueous KOH solution, or a mixture of an aqueous $NH_4(OH)$ solution and an aqueous NaOH solution is added to the aqueous solution of the metal nitrate mixture. That is, the basic aqueous solution or mixture is added to the aqueous solution of the binary metal nitrate mixture.

In step 2, a basic aqueous solution or mixture is preferably added with stirring. Specifically, an aqueous NaOH solution, an aqueous KOH solution, or a mixture of an aqueous $NH_4$(OH) solution and an aqueous NaOH solution may be added dropwise at a rate of 2 ml/min while stirring the aqueous solution of the metal nitrate mixture.

In step 2, when the aqueous NaOH solution is added alone, it preferably has a concentration of 0.5 to 2.0 M. The addition of the aqueous NaOH solution having a concentration below the lower limit causes incomplete precipitation of the metal salts. Meanwhile, the addition of the aqueous NaOH solution having a concentration above the upper limit makes it difficult to remove unreacted NaOH in the subsequent step.

In step 2, when the aqueous KOH solution is added alone, it preferably has a concentration of 0.5 to 2.0 M. The addition of the aqueous KOH solution having a concentration below the lower limit causes incomplete precipitation of the metal salts. Meanwhile, the addition of the aqueous KOH solution having a concentration above the upper limit makes it difficult to remove unreacted KOH in the subsequent step.

In step 2, when the mixture of an aqueous $NH_4(OH)$ solution and an aqueous NaOH solution is added, it is preferred that the $NH_4(OH)$ is present at a concentration of 0.1 to 0.5 M and the NaOH is present at a concentration of 0.5 to 1.5 M. If the $NH_4(OH)$ concentration is below the lower limit, addition of the $NH_4(OH)$ has little or no effect. Meanwhile, if the $NH_4(OH)$ concentration is above the upper limit, the effect of adding the $NH_4(OH)$ is negligible. If the NaOH concentration is below the lower limit, the metal salts are incompletely precipitated. Meanwhile, if the NaOH concentration is above the upper limit, it is difficult to remove unreacted NaOH in the subsequent step.

In step 3, the mixture of step 2 is aged. That is, the mixture of the aqueous solution of the metal nitrate mixture and the basic aqueous solution is aged to induce the formation of a binary metal compound of zinc and aluminum.

In step 3, the aging is preferably performed with stirring.

In step 3, the aging is preferably performed at a temperature of 50 to 70° C. If the aging temperature is below the lower limit, the time required for the aging is extended. Meanwhile, if the aging temperature is above the upper limit, aging effects are unsatisfactory.

In step 3, the aging is preferably performed for a time of 12 to 24 hours. If the aging time is shorter than the lower limit, the aging effects are reduced. Meanwhile, if the aging time is longer than the upper limit, the time required to produce a final catalyst is extended.

In step 4, the aged mixture is filtered and washed to obtain a solid. That is, the solid formed in the previous aging step is separated by filtration and washing.

The filtration and washing can be performed by general methods know in the art. Specifically, the filtration can be performed using a filter paper and the washing may be performed using deionized water.

The method of the present invention may further include drying the wet solid (step 4-1) after step 4 and prior to step 5.

The drying is preferably performed at a temperature of 80 to 120° C. for 12 to 48 hours.

In step 5, the solid is calcined under an oxygen, nitrogen or helium atmosphere. That is, the binary metal compound of zinc and aluminum obtained in the previous step is calcined under a particular gas atmosphere to obtain a catalyst.

In step 5, the calcining is preferably performed at a temperature of 400 to 500° C. A calcining temperature below the lower limit decreases the degree of crystallization of the metal oxide. Meanwhile, a calcining temperature above the upper limit decreases the specific surface area of the catalyst, leading to poor activity of the catalyst.

In step 5, the calcining is preferably performed for a time of 3 to 9 hours. If the calcining time is shorter than the lower limit, the degree of crystallization of the catalyst is lowered. Meanwhile, if the calcining time is longer than the upper limit, the time required to produce the catalyst is extended.

Each of the densities of acid sites and base sites on the surface of the catalyst produced by the method of the present invention is preferably at least 5. If either the density of acid sites or the density of base sites is lower than 5, suitable activity of the catalyst cannot be exhibited.

According to another aspect of the present invention, there is provided a catalyst for synthesizing glycerol carbonate from glycerol, which is produced by the method.

According to yet another aspect of the present invention, there is provided a method for preparing glycerol carbonate, including 1) reacting glycerol with urea in the presence of the catalyst to prepare glycerol carbonate (step 1); and 2) collecting the glycerol carbonate (step 2).

In step 1, glycerol is reacted with urea in the presence of the catalyst to prepare glycerol carbonate. That is, glycerol is converted to glycerol carbonate by a urea conversion process in the presence of the catalyst to prepare glycerol carbonate.

As a result of the reaction of glycerol with urea in the presence of the catalyst in the glycerol carbonate preparation method of the present invention, high conversion rate of glycerol, high selectivity to glycerol carbonate, and the resulting high yield of glycerol carbonate are achieved.

The term "conversion rate of glycerol" as used herein means the proportion of the total amount of products obtained as a result of the conversion reaction in the presence of the catalyst, based on the initial amount of glycerol as a starting material. That is, the term means the proportion of reaction products converted from the starting material glycerol.

The term "selectivity to glycerol carbonate" as used herein means the proportion of the amount of the desired reaction product relative to the initial amount of glycerol. That is, the term means the proportion of glycerol carbonate converted from glycerol.

The term "yield of glycerol carbonate" as used herein means the yield of glycerol carbonate obtained as a result of the reaction in the presence of the catalyst. The yield of glycerol carbonate is expressed as a product of the conversion rate of glycerol and the selectivity to glycerol carbonate.

The conversion rate of glycerol in step 1 is from 80 to 85%. Specifically, the conversion rate of glycerol as a result of the reaction in the presence of a catalyst produced by an embodiment of the present invention is 82.7%.

The selectivity to glycerol carbonate in step 1 is from 90 to 99.9%. Specifically, the selectivity to glycerol carbonate as a result of the reaction in the presence of a catalyst produced by an embodiment of the present invention is 99.5%.

The yield of glycerol carbonate in step 1 is from 73 to 83%. Specifically, the yield of glycerol carbonate as a result of the reaction in the presence of a catalyst produced by an embodiment of the present invention is 82.3%.

In step 1, the molar ratio of glycerol to urea is preferably from 1:5 to 5:1, more preferably from 1:2 to 2:1, most preferably 1:1.

In step 1, the catalyst is preferably used in an amount of 1 to 10% by weight, more preferably 3 to 7% by weight, most preferably 5% by weight, based on the weight of glycerol.

In step 1, the reaction is preferably carried out at a temperature of 100 to 180° C., more preferably 120 to 160° C., most preferably 140° C. If the reaction temperature is outside the range defined above, the reaction is incomplete or undesirable side reactions occur.

In step 1, the reaction is preferably carried out for 1 to 10 hours, more preferably 3 to 7 hours, most preferably 5 hour. If the reaction time is outside the range defined above, the reaction is incomplete or undesirable side reactions occur.

In step 1, the reaction is preferably carried out under vacuum conditions. Specifically, the reaction pressure is preferably from 1 to 10 kPa, more preferably from 2 to 6 kPa, most preferably 4 kPa.

In step 2, the glycerol carbonate is collected. That is, the glycerol carbonate prepared as a result of the reaction in step 1 is collected.

In the present invention, the glycerol carbonate may be collected by any suitable method known in the art.

The constitutions of the present invention will now be described in detail with reference to the accompanying drawings.

FIG. 1 is a flow chart illustrating the steps of a method for producing a catalyst suitable for the synthesis of glycerol carbonate from glycerol according to a preferred embodiment of the present invention.

As illustrated in FIG. 1, the method includes preparing an aqueous solution of a mixture of zinc nitrate and aluminum nitrate (step 1), adding an aqueous NaOH solution, an aqueous KOH solution, or a mixture of an aqueous $NH_4(OH)$ solution and an aqueous NaOH solution to the aqueous solution of the metal nitrate mixture (step 2), aging the mixture of step 2 (step 3), filtering and washing the aged mixture to obtain a solid (step 4), and calcining the solid under an oxygen, nitrogen or helium atmosphere (step 5).

According to the method of the present invention, a catalyst in the form of a binary metal oxide composed of zinc (Zn) as a base element and aluminum (Al) as a secondary element can be produced. The ratio of the density of acid sites to that of base sites on the catalyst surface is from 0.3 to 2.0. The catalyst can be used for the conversion of glycerol to glycerol carbonate using a urea conversion process. Specifically, the catalyst in the form of a binary metal oxide has both acid sites and base sites. The metals, i.e. zinc and aluminum, present in the catalyst act as Lewis acid sites and are bonded to the carbonyl group of the urea. The oxygen atoms present in the catalyst in the form of a binary metal oxide act as Lewis base sites and are bonded the terminal hydroxyl groups of the glycerol. As a result of the reaction of the glycerol and the urea, glycerol urethane is formed as an intermediate of glycerol carbonate. Finally, the catalyst induces the intramolecular reaction of the glycerol urethane to give glycerol carbonate.

The conversion of glycerol to glycerol carbonate using urea is depicted in Reaction Scheme 1:

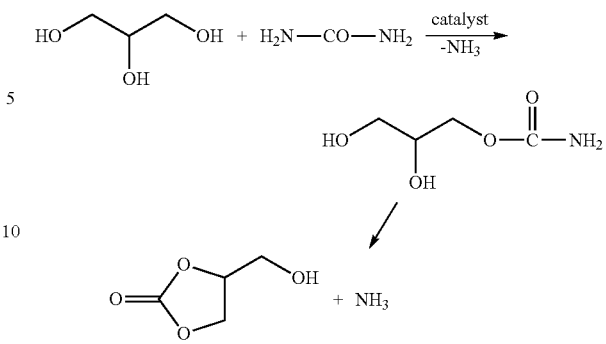

The molar ratio of metal elements in an inorganic catalyst and the crystal morphology of the inorganic catalyst may be varied depending on reaction factors of a method for the production of the inorganic catalyst. The reaction factors may also affect the activity of the catalyst.

The catalyst produced by the method of the present invention has high conversion rate of glycerol, selectivity to glycerol carbonate and the resulting high yield of glycerol carbonate, thus being suitable for the synthesis of glycerol carbonate from glycerol.

Specifically, the method of the present invention is characterized by the addition of an aqueous NaOH solution, an aqueous KOH solution, or a mixture of an aqueous $NH_4(OH)$ solution and an aqueous NaOH solution as a basic material to an aqueous solution of a metal nitrate mixture, and calcination of a solid under an oxygen, nitrogen or helium atmosphere in the final step, thus enabling the production of a highly active catalyst.

According to the method of the present invention, a catalyst for synthesizing glycerol carbonate from glycerol can be produced by adding an aqueous NaOH solution, an aqueous KOH solution, or a mixture of an aqueous $NH_4(OH)$ solution and an aqueous NaOH solution to an aqueous solution of a mixture of zinc nitrate and aluminum nitrate, aging the mixture, filtering and washing the aged mixture to obtain a solid, and calcining the solid under an oxygen, nitrogen or helium atmosphere. The catalyst can promote the reaction due to the presence of both acid sites and base sites. By the use of the catalyst, glycerol carbonate can be synthesized from glycerol with high conversion rate, selectivity and yield.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

The present invention will be explained in detail with reference to the following examples. These examples are provided to assist in further understanding of the invention and are not intended to limit the scope of the invention.

EXAMPLES

Examples 1-5

Production of Catalysts Using Zn/Al in Different Molar Ratios

To 1,000 ml of water were added $Zn(NO_3)_2 \cdot 6H_2O$ and $Al(NO_3)_3 \cdot 9H_2O$ in different molar ratios shown in Table 1 to prepare aqueous solutions of the metal nitrate mixtures. Thereafter, a 1.0 M aqueous NaOH solution was added to each of the aqueous solutions of the metal nitrate mixtures with stirring.

Then, the resulting mixture was aged with stirring at 60° C. for 12 hr. The aged mixture was filtered and washed with deionized water to obtain a solid. The solid was dried at 100° C. for 24 hr. Finally, the dried solid was calcined at 450° C. under an oxygen atmosphere to produce a catalyst.

TABLE 1

| Example No. | Moles | |
| --- | --- | --- |
| | Zn | Al |
| Example 1 | 10 | 0 |
| Example 2 | 9 | 1 |
| Example 3 | 8 | 2 |
| Example 4 | 7 | 3 |
| Example 5 | 5 | 5 |

Examples 6-10

Production of Catalysts Using Different Kinds and Concentrations of Basic Materials Catalysts were produced in the same manner as in Example 4, except that an aqueous NaOH solution (Examples 6 and 7), an aqueous KOH solution (Examples 8 and 9), and a mixture of an aqueous $NH_4(OH)$ solution and an aqueous NaOH solution (Example 10) having the concentrations shown in Table 2 were added to the aqueous solution of the metal nitrate mixture, instead of the 1.0 M aqueous NaOH solution.

TABLE 2

| | Concentrations | | |
| --- | --- | --- | --- |
| Example No. | Aqueous NaOH solution (M) | Aqueous KOH solution (M) | Aqueous $NH_4(OH)$ solution (M) |
| Example 6 | 1.5 | 0 | 0 |
| Example 7 | 2.0 | 0 | 0 |
| Example 8 | 0 | 0.5 | 0 |
| Example 9 | 0 | 1.5 | 0 |
| Example 10 | 0.5 | 0 | 0.5 |

Examples 11-12

Production of Catalysts Under Different Calcining Atmospheres

Catalysts were produced in the same manner as in Example 4, except that the calcining atmosphere was changed from an oxygen atmosphere to a nitrogen atmosphere (Example 11) and a helium (Example 12) atmosphere.

Examples 13-17

Production of Catalysts at Different Calcining Temperatures

Catalysts were produced in the same manner as in Example 4, except that the calcining temperature was changed from 450° C. to 400° C. (Example 13), 500° C. (Example 14), 600° C. (Example 15), 700° C. (Example 16), and 800° C. (Example 17).

Experimental Example 1

Investigation of Morphologies of the Catalysts

The crystal phases of the catalysts produced in Examples 2-5 and Examples 13-17 were investigated using an X-ray diffractometer (XRD, PHILLIPS X'Pert-MPD System, Netherlands).

Figure 1:
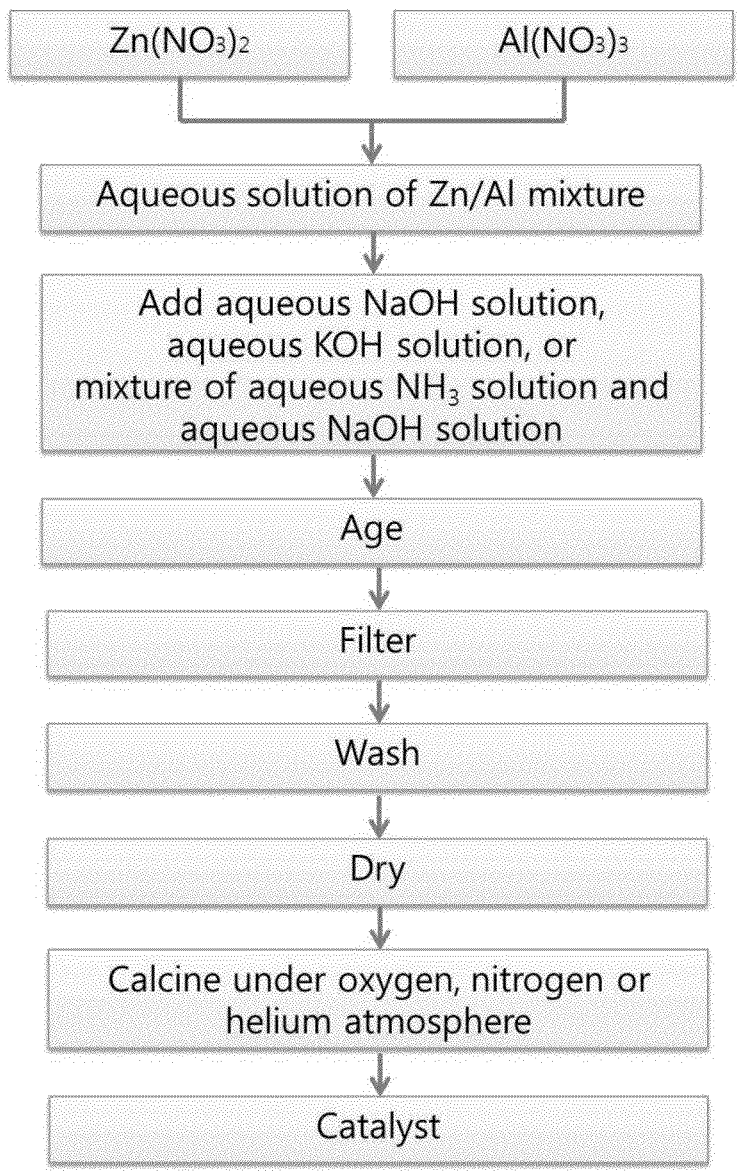
FIG. 1 is a flow chart illustrating the steps of a catalyst production method according to the present invention.
Figure 2:
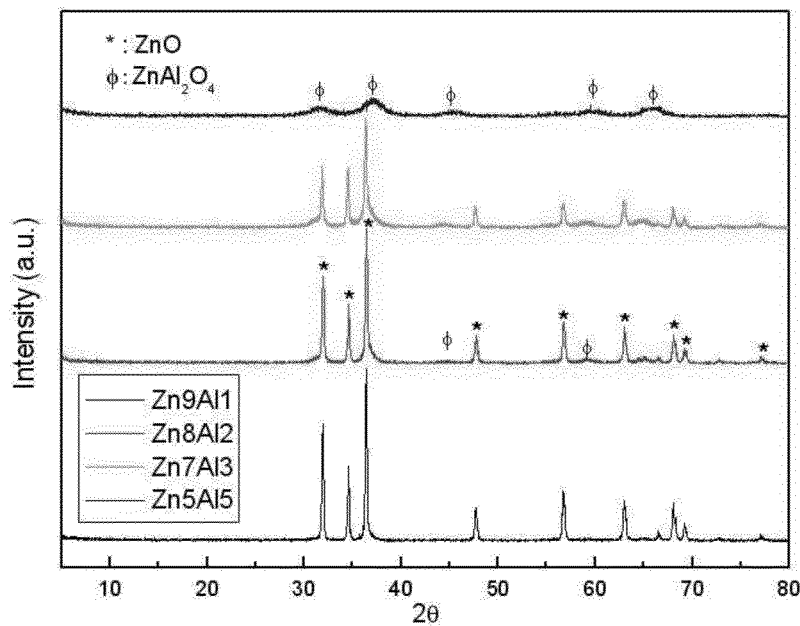
FIG. 2 shows XRD patterns of catalysts produced in Examples 1 to 5.
Figure 3:
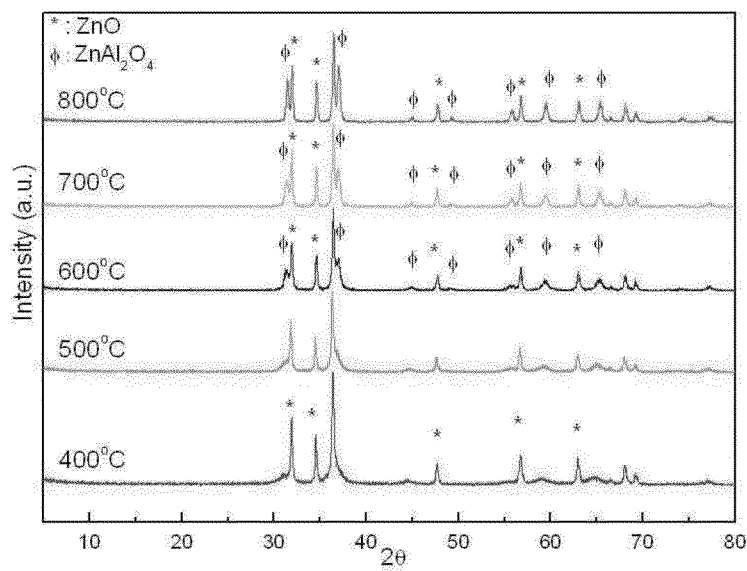
FIG. 3 shows XRD patterns of catalysts produced in Examples 13 to 17.

The results are shown in FIGS. 2 and 3.

As shown in FIG. 2, the catalysts produced in Examples 2-5 had different characteristic crystal peaks, demonstrating different crystal phases of the catalysts with varying Zn/Al molar ratios.

As shown in FIG. 3, the catalysts produced in Examples 13-17 had different characteristic crystal peaks, demonstrating different crystal phases of the catalysts with varying calcining temperatures.

The morphologies of the catalysts produced in Examples 2-5 and Examples 13-17 were observed by scanning electron microscopy (SEM). The SEM images were taken using a field emission scanning electron microscopy (FE-SEM, JEOL JSM-6700, JAPAN).

Figure 4:
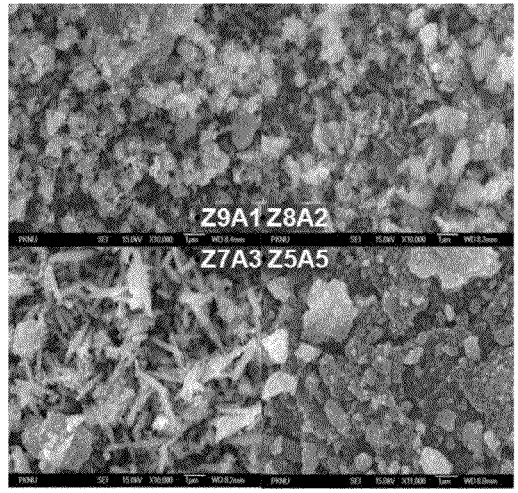
FIG. 4 shows FE-SEM images of catalysts produced in Examples 1 to 5.
Figure 5:
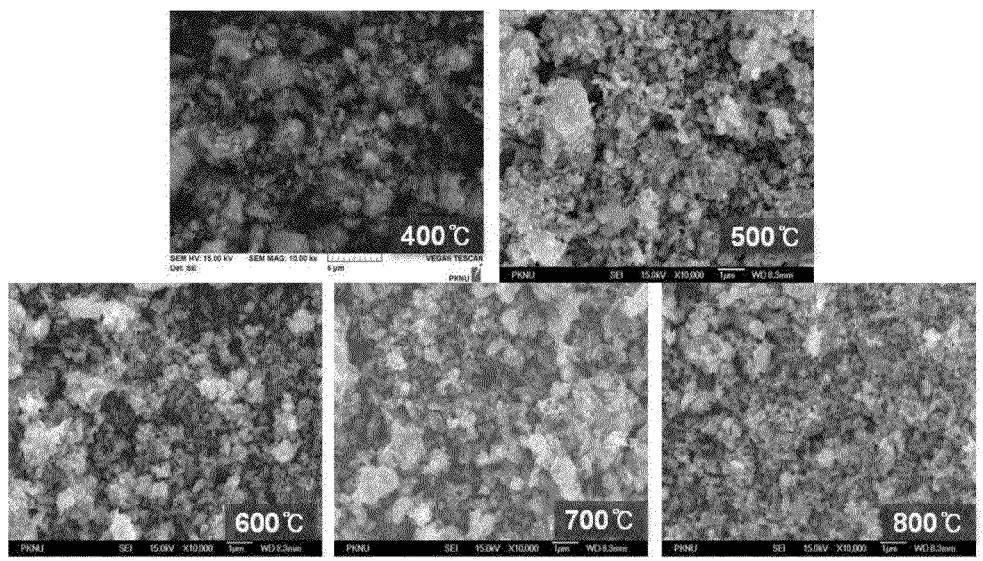
FIG. 5 shows FE-SEM images of catalysts produced in Examples 13 to 17.

The results are shown in FIGS. 4 and 5.

As can be seen from FIG. 4, the catalysts produced in Examples 2-5 had well-defined fine particles. Particularly, the catalyst of Example 4 was found to have needle-like fine particles.

As can be seen from FIG. 5, the catalysts produced in Examples 13-17 had well-defined fine particles.

Experimental Example 2

Analysis of Surface Characteristics of the Catalysts

The specific surface areas of the catalysts produced in Examples 2-5 and Examples 13-17 were measured using a surface area analyzer (Micromeritics ASAP 2010, USA) by the Brunauer-Emmett-Teller (BET) method.

The catalysts produced in Examples 2-5 and Examples 13-17 were analyzed by temperature programmed desorption (TPD) to determine the densities of Lewis acid sites, the densities of Lewis base sites and ratios thereof in the catalysts. The densities of Lewis acid sites were determined by TPD analysis of $NH_3$ and the densities of Lewis base sites were determined by TPD analysis of $CO_2$. The ratios of the Lewis acid sites to the Lewis base site were calculated from the determined values.

Figure 6:
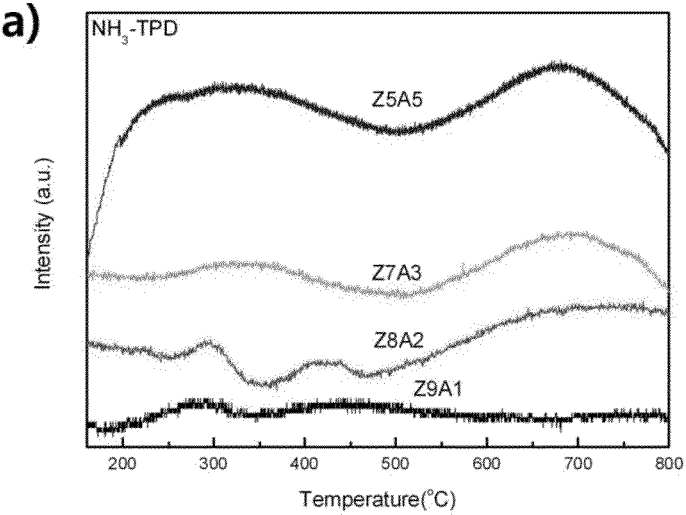
FIG. 6 shows the results of temperature programmed desorption (TPD) for catalysts produced in Examples 1 to 5: a) shows the densities of Lewis acid sites measured by TPD of $NH_3$, and b) shows the densities of Lewis base sites measured by TPD of $CO_2$.
Figure 6:
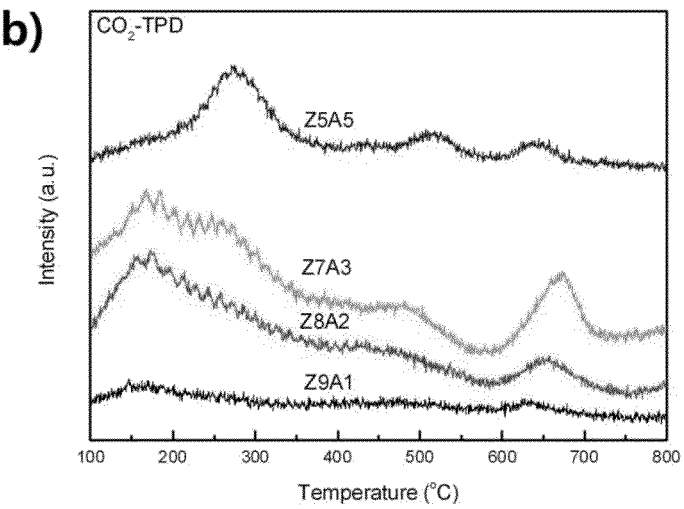
Figure 7:
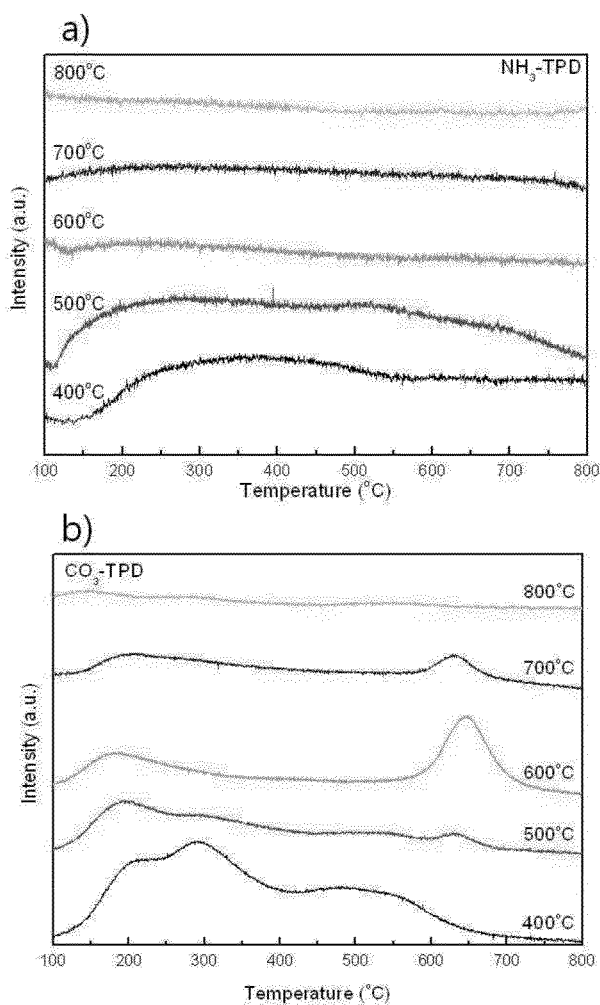
FIG. 7 shows the results of temperature programmed desorption (TPD) for catalysts produced in Examples 13 to 17: a) shows the densities of Lewis acid sites measured by TPD of $NH_3$, and b) shows the densities of Lewis base sites measured by TPD of $CO_2$.

The results are shown in Tables 3-4 and FIGS. 6-7.

TABLE 3

| Example No. | Specific surface area (m²/g) | Density of acid sites (μmol/g) | Density of base sites (μmol/g) | Acid/base ratio |
| --- | --- | --- | --- | --- |
| Example 2 | 20.60 | 7.61 | 1.86 | 4.09 |
| Example 3 | 38.17 | 9.93 | 5.41 | 1.84 |
| Example 4 | 34.73 | 6.24 | 7.15 | 0.87 |
| Example 5 | 219.71 | 12.03 | 2.92 | 4.12 |

As can be seen from the results in Table 3 and FIG. 6, the catalysts had different specific surface areas with varying molar ratios of Zn/Al. Further, the densities of Lewis acid sites, the densities of Lewis base sites and acid/base ratios were significantly varied. Referring to the results in Table 3, the acid/base ratios in the catalysts of Examples 3 and 4 were approximated 1. Further, the densities of acid sites and the densities of base sites in the catalysts of Examples 3 and 4 were above 5, demonstrating the presence of active points in the catalysts. Particularly, the catalyst of Example 4 in which Zn and Al were present in a molar ratio of 7:3 had an acid/base ratio closest to 1.

TABLE 4

| Example No. | Density of acid sites (μmol/g) | Density of base sites (μmol/g) | Acid/base ratio |
| --- | --- | --- | --- |
| Example 13 | 6.83 | 17.71 | 0.3857 |
| Example 14 | 8.03 | 8.70 | 0.9230 |
| Example 15 | 3.03 | 9.23 | 0.3283 |
| Example 16 | 2.41 | 8.74 | 0.2757 |
| Example 17 | 2.00 | 3.67 | 0.5450 |

As can be seen from the results in Table 4 and FIG. 7, the densities of Lewis acid sites, the densities of Lewis base sites and acid/base ratios were significantly varied. These results are explained by different degrees of crystallization of the catalysts at various calcining temperatures. Tables 4 and FIG. 7 reveal that active points were observed at calcining temperatures up to 700° C. for the densities of base sites and only at calcining temperatures up to 500° C. for the densities of acid sites. Particularly, the catalyst of Example 14, which was produced at a calcining temperature of 500° C., had an acid/base ratio closest to 1.

Examples 18-34

Preparation of Glycerol Carbonate Using the Catalysts

Glycerol was reacted with urea in the presence of each of the catalysts produced in Examples 1-17 to prepare glycerol carbonate.

A reactor equipped with a condenser system and a vacuum pump was used for the preparation of glycerol carbonate. Glycerol, urea and the catalyst were placed in the reactor and were allowed to react with stirring at 140° C. and 4 kPa for 5 hr. The glycerol and the urea were used in a molar ratio of 1:1. The catalyst was used in an amount of 5 wt %, based on the weight of the glycerol.

After completion of the reaction, the reaction mixture was filtered and the catalyst was washed with acetone to collect the product from the catalyst surface. The filtrate and the washing solution were collected and concentrated under reduced pressure, yielding glycerol carbonate.

Experimental Example 3

Determination of Conversion Rate of Glycerol, Selectivity to Glycerol Carbonate and Yield of Glycerol Carbonate in the Glycerol Carbonate Preparation Method of the Present Invention The conversion rate of glycerol, selectivity to glycerol carbonate, and yield of glycerol carbonate were determined after the preparation of glycerol carbonate in Examples 18-34.

Figure 8:
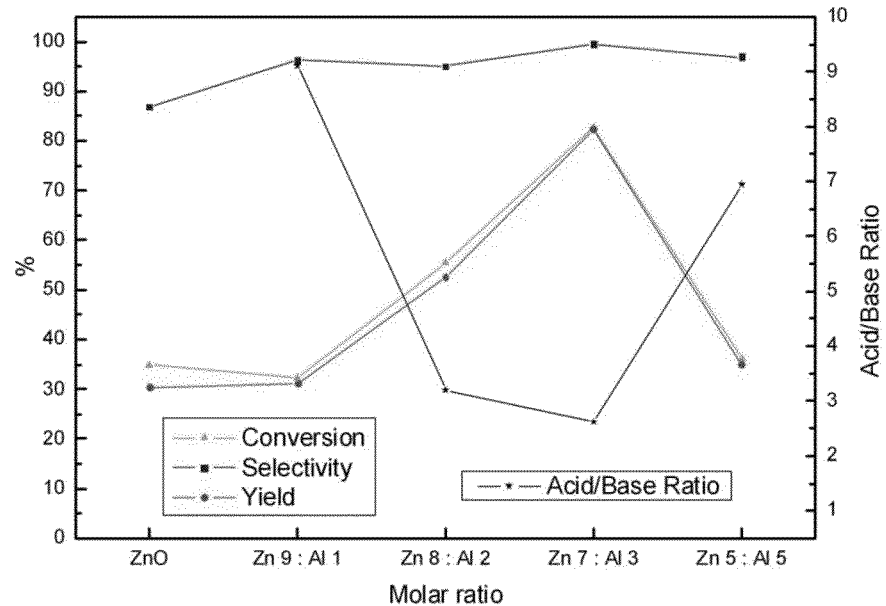
FIG. 8 shows changes in the conversion rate of glycerol, the selectivity to glycerol carbonate and the yield of glycerol carbonate with varying acid/base ratios in catalysts used for the preparation of glycerol carbonate in Examples 18 to 22.
Figure 9:
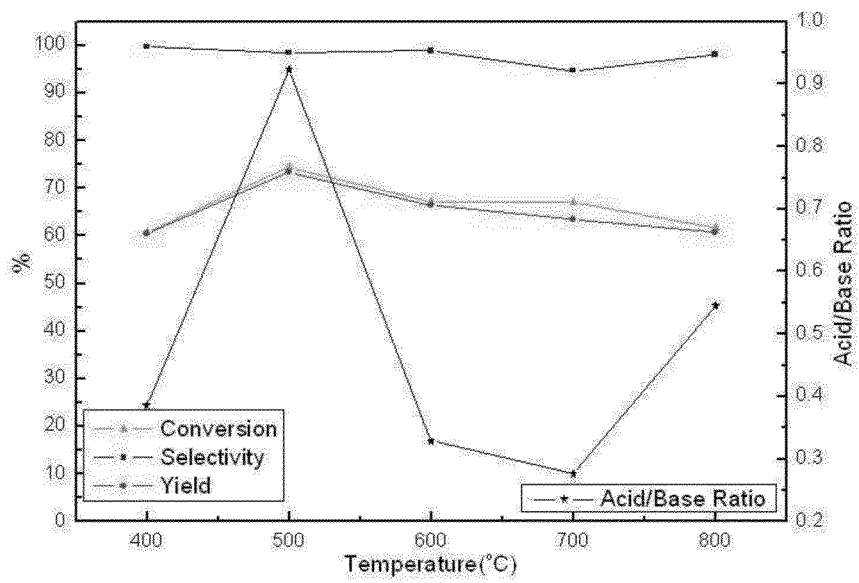
FIG. 9 shows changes in the conversion rate of glycerol, the selectivity to glycerol carbonate and the yield of glycerol carbonate with varying acid/base ratios in catalysts used for the preparation of glycerol carbonate in Examples 30 to 34.

The results are shown in Table 5 and FIGS. 8 and 9. The acid/base ratios in the catalysts are also shown in Table 5 and FIGS. 8 and 9 to investigate correlations thereof with the conversion rate of glycerol, selectivity to glycerol carbonate, and yield of glycerol carbonate. FIG. 8 shows the results in Examples 18-22 and FIG. 9 shows the results in Examples 30-34.

TABLE 5

| Example No. | Conversion rate (%) | Selectivity (%) | Yield (%) | Acid/base ratio |
| --- | --- | --- | --- | --- |
| Example 18 | 34.9 | 86.9 | 30.4 | — |
| Example 19 | 32.3 | 96.3 | 31.1 | 4.09 |
| Example 20 | 55.3 | 95.1 | 52.6 | 1.84 |
| Example 21 | 82.7 | 99.5 | 82.3 | 0.87 |
| Example 22 | 36 | 96.9 | 34.9 | 4.12 |
| Example 23 | 77.4 | 85.8 | 66.4 | |
| Example 24 | 79.2 | 86.0 | 68.1 | |
| Example 25 | 76.7 | 84.6 | 64.9 | |
| Example 26 | 79.8 | 82.8 | 66.1 | |
| Example 27 | 82.1 | 88.4 | 72.6 | |
| Example 28 | 80.7 | 88.6 | 71.5 | |
| Example 29 | 84.3 | 86.7 | 73.1 | |
| Example 30 | 60.7 | 99.7 | 60.5 | 0.3857 |
| Example 31 | 74.4 | 98.4 | 73.3 | 0.9293 |
| Example 32 | 67.1 | 98.9 | 66.4 | 0.3283 |
| Example 33 | 67.0 | 94.7 | 63.4 | 0.2757 |
| Example 34 | 61.8 | 98.0 | 60.6 | 0.5450 |

As can be seen from Table 5 and FIGS. 8 and 9, the conversion rates and yields were increased as the acid/base ratios were close to 1. That is, the highest activity of the catalysts is obtained in an acid/base ratio of 1. Specifically, the glycerol carbonate conversion rates were significantly high and the resulting glycerol carbonate yields were significantly high when the catalyst of Example 4 was used to prepare glycerol carbonate in Example 21 and the catalyst of Example 14 was used to prepare glycerol carbonate in Example 31, in comparison with the results obtained in the other examples. In addition, when the catalyst of Example 4 was used to prepare glycerol carbonate in Example 21, both conversion rate and selectivity were high, indicating a markedly increased yield of glycerol carbonate.

What is claimed is:

1. A method for producing a catalyst suitable for the synthesis of glycerol carbonate from glycerol, the method comprising
preparing an aqueous solution of a mixture of zinc nitrate and aluminum nitrate (step 1),
adding an aqueous NaOH solution, an aqueous KOH solution, or a mixture of an aqueous $NH_4(OH)$ solution and an aqueous NaOH solution to the aqueous solution of the metal nitrate mixture (step 2),
aging the mixture of step 2 (step 3),
filtering and washing the aged mixture to obtain a solid (step 4), and
calcining the solid under an oxygen, nitrogen or helium atmosphere to produce a catalyst (step 5),
wherein the ratio of the density of acid sites to that of base sites on the catalyst surface is from 0.3 to 2.0 and
wherein the mixing molar ratio of the zinc to the aluminum is adjusted to 7:3 to 8:2.

2. The method according to claim 1, wherein when the aqueous NaOH solution is added alone in step 2, it has a concentration of 0.5 to 2.0 M.

3. The method according to claim 1, wherein when the aqueous KOH solution is added alone in step 2, it has a concentration of 0.5 to 2.0 M.

4. The method according to claim 1, wherein when the mixture of an aqueous $NH_4(OH)$ solution and an aqueous NaOH solution is added in step 2, the aqueous $NH_4(OH)$ solution has a concentration of 0.1 to 0.5 M and the aqueous NaOH solution has a concentration of 0.5 to 1.5 M.

5. The method according to claim 1, wherein, in step 3, the aging is performed at a temperature of 50 to 70° C.

6. The method according to claim 1, wherein, in step 5, the calcining is performed at a temperature of 400 to 500° C.

7. The method according to claim 1, wherein, in step 5, the calcining is performed for 3 to 9 hours.

8. The method according to claim 1, wherein each of the densities of acid sites and base sites on the catalyst surface is at least 5.

9. A catalyst for synthesizing glycerol carbonate from glycerol wherein the catalyst is produced by the method according to claim 1.

10. A method for preparing glycerol carbonate, the method comprising
reacting glycerol with urea in the presence of the catalyst according to claim 9 to prepare glycerol carbonate (step 1), and
collecting the glycerol carbonate (step 2).

11. The method according to claim 10, wherein the selectivity to glycerol carbonate in the reaction of step 1 is from 90 to 99.9%.

12. The method according to claim 10, wherein the yield of glycerol carbonate in the reaction of step 1 is from 73 to 83%.

* * * * *